United States Patent
Yoon et al.

(10) Patent No.: US 8,194,154 B2
(45) Date of Patent: Jun. 5, 2012

(54) PORTABLE VIDEO MAGNIFYING APPARATUS

(75) Inventors: Yang Taik Yoon, Daejeon (KR); Kyeong Seon Choi, Daejeon (KR); Il Hyung Kim, Daejeon (KR); Wock Lyul Lee, Daejeon (KR)

(73) Assignee: Hims International Corporation, Daejeon (KR)

( * ) Notice: Subject to any disclaimer, the term of this patent is extended or adjusted under 35 U.S.C. 154(b) by 410 days.

(21) Appl. No.: 12/446,419

(22) PCT Filed: Nov. 23, 2007

(86) PCT No.: PCT/KR2007/005956
§ 371 (c)(1),
(2), (4) Date: Apr. 20, 2009

(87) PCT Pub. No.: WO2009/066819
PCT Pub. Date: May 28, 2009

(65) Prior Publication Data
US 2010/0321526 A1 Dec. 23, 2010

(51) Int. Cl.
H04N 5/76 (2006.01)
H04N 5/222 (2006.01)
H04N 5/225 (2006.01)
H04B 1/38 (2006.01)
H04M 1/00 (2006.01)

(52) U.S. Cl. ............... 348/231.2; 348/372; 348/375; 348/333.01; 455/90; 455/556.1

(58) Field of Classification Search ............ 348/211.11–211.13, 373–374, 348/262, 48, 153, 159
See application file for complete search history.

(56) References Cited

U.S. PATENT DOCUMENTS

| | | | |
|---|---|---|---|
| 6,750,890 B1 * | 6/2004 | Sugimoto | 715/838 |
| 7,286,306 B2 | 10/2007 | Wu | |
| 7,365,794 B2 * | 4/2008 | Yasui | 348/374 |
| 7,616,236 B2 * | 11/2009 | Bae | 348/240.99 |
| 7,764,320 B1 * | 7/2010 | Salvato | 348/344 |
| 7,855,747 B2 * | 12/2010 | Jang et al. | 348/372 |
| 2003/0036365 A1 * | 2/2003 | Kuroda | 455/90 |
| 2006/0034601 A1 * | 2/2006 | Andersson et al. | 396/157 |
| 2006/0146167 A1 * | 7/2006 | Aizawa et al. | 348/333.01 |
| 2008/0058010 A1 * | 3/2008 | Lee | 455/556.1 |

FOREIGN PATENT DOCUMENTS

EP 0563541 A1 10/1993

* cited by examiner

*Primary Examiner* — Jason Chan
*Assistant Examiner* — Pritham Prabhakher
(74) *Attorney, Agent, or Firm* — The Webb Law Firm

(57) ABSTRACT

Disclosed is a portable video magnifying apparatus. The video magnifying apparatus of the present invention comprises a main frame; a short distance image detecting part which is pivotably disposed at the main frame so as to allow proximity photographing with respect to a subject on a right under surface of the short distance image detecting part or therearound; a long distance image detecting part which is provided with a long distance photographing lens for photographing a long distance subject and which is disposed at the main frame; and a display part which outputs one out of the short distance image, the long distance image and an image input through an external portion, which is selected by a user. Therefore, it is possible to help the weak-sighted or aged person.

14 Claims, 11 Drawing Sheets

PORTABLE VIDEO MAGNIFYING APPARATUS

TECHNICAL FIELD

The present invention relates to a portable video magnifying apparatus, more particularly, to a portable video magnifying apparatus for a weak-sighted or aged person, which can convert an image detected by a long and short distance image detecting part into a desired image such as magnified, color-converted and still images, and then adapt the image to be output through a display part.

BACKGROUND ART

In general, a visually handicapped person means man who loses one's sight and optical sense due to an eye disease and thus can not tell even the brightness and darkness, and also includes man who has very weak sight and thus can discriminate the brightness and darkness and recognize movement of a hand before one's eye. The weak-sighted persons who have a majority among the visually handicapped persons can not recognize a subject like a character or a diagram using general glasses or contact lens due to weakening of the lens, iris, retina and visual nervous system.

A portable video magnifying apparatus is to magnify an image of a subject such as small characters in a book, a phial, a check or currency and the like, which are difficult to see, and thus assist the defective vision of the weak-sighted person and the aged person. The portable video magnifying apparatus is provided with a rechargeable battery and can be used in any place even where a power line can not be connected, so that the weak-sighted person and the aged person can see exactly the subject.

However, in a conventional portable video magnifying apparatus, to see a distant subject, a user should go near the subject, and also even though the user goes near the subject, if the subject is positioned at a higher place than user's eye level, the user can not make certain the subject. In order to make certain the subject, the user should ask other person for help. Alternatively, since the user has to prepare a separate distant video magnifying apparatus like a telescope, it is an economical burden and also it is inconvenient to carry it. Further, since it is difficult to notice a position of a photographing lens which is placed at a lower surface of a display part, it takes unnecessary time to find the position of the subject. And also there is an inconvenience in that when the user writes something, the user should obliquely take the portable video magnifying apparatus in one hand so that the photographing lens is directed to the subject so as to check it.

Therefore, there arises the necessity for unifying long and short distance image detecting parts to save a space. Further, image pausing and storing functions are required in order to check the subject positioned at a higher place than the eye level, and the position of the photographing lens has to be capable of easily recognized by the user so that the position of the subject can be found rapidly. And when the user writes something, in order to check it, only the short distance image detecting part has to be capable of being pivoted while the portable video magnifying apparatus is put therearound. Furthermore, the portable video magnifying apparatus has to be capable of being connected with TV, and TV images can be output through the portable video magnifying apparatus so as to help the weak-sighted person who has a narrow viewing angle and thus can not see the whole screen.

DISCLOSURE

Technical Problem

An object of the present invention is to provide a portable video magnifying apparatus in which long and short distance image detecting parts are unified.

Another object of the present invention is to provide a portable video magnifying apparatus which has an image pausing and storing function for checking the subject positioned at a higher place than the eye level.

Yet another object of the present invention is to provide a portable video magnifying apparatus in which a position of a photographing lens can be easily recognized by a user so that the user can find a subject, and when the user writes something, it is possible to check it in a state that the portable video magnifying apparatus is put therearound.

Yet another object of the present invention is to provide a portable video magnifying apparatus which can be connected with TV, and TV images can be output through the portable video magnifying apparatus so as to help the weak-sighted person who has a narrow viewing angle and thus can not see the whole screen.

Technical Solution

To achieve the above-mentioned objects, there is provided a portable video magnifying apparatus, comprising a main frame 100; a short distance image detecting part 200 which is pivotably disposed at the main frame 100 so as to photograph proximately a subject placed right under the main frame 100 or around there; a long distance image detecting part 300 which is provided with a long distance photographing lens 310 for photographing a long distance subject and which is disposed at the main frame 100; and a display part 400 which outputs one out of the short distance image, the long distance image and an image input through an external portion, which is selected by a user.

Preferably, the short distance image detecting part 200 comprises an auxiliary frame 210 which is pivotably disposed at the main frame 100; a short distance photographing lens 220 which is disposed at the auxiliary frame 210 so as to photograph proximately a subject placed right under the main frame 100 or around there; an illuminating LED 230 which is disposed around the short distance photographing lens 220 so as to illuminate the subject upon a photographing operation; and a short distance camera indicating lamp 240 which is disposed on an opposite surface of the short distance photographing lens 220 so as to inform the user of activation of the short distance image detecting part 200. And the auxiliary frame 210 is positioned in a reading mode so that a surface thereof having the short distance photographing lens 220 is placed at an upper side of a lower surface of the main frame 100, and the auxiliary frame 210 is rotated at a desired angle in a writing mode so that the surface thereof having the short distance photographing lens 220 is directed to an outer side of the main frame 100. And, the long distance image detecting part 300 comprises a focus adjusting part 320 which is rotated clockwise or counterclockwise so as to adjust a focus of the long distance photographing lens 310; and a long distance camera indicating lamp 330 which is disposed on an opposite surface of the long distance photographing lens 310 so as to inform the user of activation of the long distance image detecting part 300, and the long distance image detecting part 300 may further comprise an auto focusing part for automatically focusing the long distance photographing lens 310.

Preferably, the display part 400 comprises an image pausing/storing button 410 which pauses or stores an image output through the display unit 400; a menu button 420 which outputs icons for indicating functions of displaying a stored image, deleting the stored image, checking an image storing space, checking a battery residual capacity, and scrolling a screen; and a icon selecting buttons 430 which selects the output icons. And the display part 400 further comprises a brightness adjusting button 440 which adjusts a brightness of the display part 400; a color converting button 450 which converts a color of the image into other color and then outputs the image having the converted color; and magnifying and reducing buttons 460 and 470 which controls an magnification of the output image.

Preferably, if the image pausing/storing button 410 is pushed for a shorter time period than predetermined time, the age displayed on the display part 400 is paused, and if the image pausing/storing button 410 is pushed for a longer time period than the predetermined time, the image displayed on the display part 400 is stored in a memory.

Preferably, the main frame 100 is provided with a power switch 110 for turning on/off the portable video magnifying apparatus, and the power switch 110 is automatically slid from a power-on position or a power-off position to an initial position, and the power switch 110 is also constructed so that the portable video magnifying apparatus can be automatically turned off, if the power switch 110 is slid to the power-on position and then returned to the initial position and the image is not changed for the predetermined time. And the main frame 100 is provided with a composite input terminal 160 and a camera selecting switch 120, and the display part 400 selectively displays a short or long distance image by the camera selecting switch 120, and if an image is input through the composite input terminal 160, the short or long distance image is deactivated and the input image is displayed through the display part 400.

Meanwhile, the main frame comprises a first main frame in which the display part is provided, and a second main frame in which the long distance photographing lens is provided, and the second main frame is rotatably coupled to the first main frame so that a photographing direction of the long distance photographing lens can be changed. And the second main frame can be rotated at an angle of at least 180° so that the long distance photographing lens is directed to an upper or lower surface of the first main frame.

Preferably, if the second main frame is rotated while the short distance image from the short distance image detecting part is displayed through the display part, a long distance image from the long distance image detecting part is displayed through the display part. And the second main frame may be coupled to an end of the first main frame, and the second main frame may be also rotated with respect to the first main frame at a predetermined angle and then halted.

Advantageous Effects

According to the present invention, as described above, since the long and short distance image detecting parts of the portable video magnifying apparatus are unified, there is an effect that it is possible to easily operate the portable video magnifying apparatus, and the portable space and economical problems can be solved.

Further, sine the portable video magnifying apparatus has an image pausing and storing function for recognizing the subject positioned at a higher place than the eye level, it has a wider effective using range than the conventional one.

Further, since the position of the photographing lens can be easily recognized by a user so that the user can find a subject, and it is possible to check a written state while the portable video magnifying apparatus is put therearound when the user writes something, it can provide a improved convenience to the user.

Furthermore, the present invention provides other effect that the portable video magnifying apparatus can be connected with TV, and TV images can be output through the portable video magnifying apparatus so as to help the weak-sighted person who has a narrow viewing angle and thus can not see the whole screen.

DESCRIPTION OF DRAWINGS

The above and other objects, features and advantages of the present invention will become apparent from the following description of preferred embodiments given in conjunction with the accompanying drawings, in which.

DETAILED DESCRIPTION OF MAIN ELEMENTS

Figure 1:
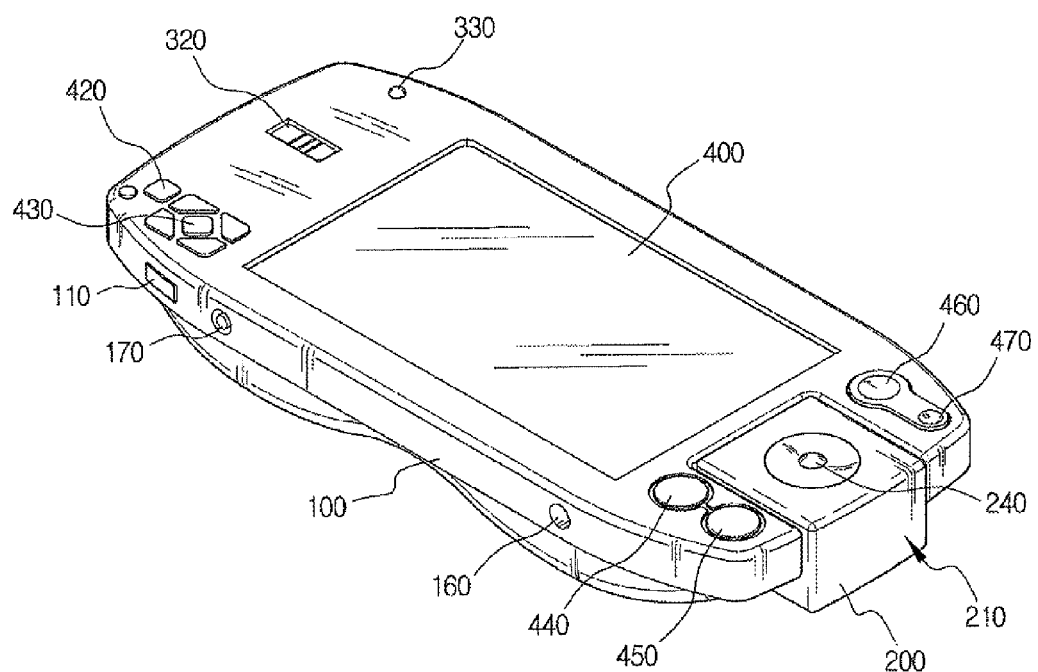
FIGS. 1 and 2 are perspective views showing a portable video magnifying apparatus according to a first embodiment of the present invention.

100: main frame
110: power switch
120: camera selecting switch
160: composite input terminal
170: power input terminal
200: short distance image detecting part
210: auxiliary frame
220: short distance photographing lens
230: illuminating LED
240: short distance camera indicating lamp
300: long distance image detecting part
310: long distance photographing lens
320: focus adjusting part 330: long distance camera indicating lamp
400: display part
410: image pausing/storing button
420: menu button
430: icon selecting button
440: brightness adjusting button
450: color converting button
460: magnifying button
470: reducing button
500: hardware system
510: composite converter
520: short distance photographing sensor
530: long distance photographing sensor
540: image selector
550: memory
560: image scaler
570: RGB format converter
580: micro-controller
590: battery
591: A/D converter
592: battery charging LED
1100: main frame
1110: first main frame
1120: second main frame
1310: long distance photographing lens
1400: display part

BEST MODE

Hereinafter, the embodiments of the present invention will be described in detail with reference to accompanying drawings.

First Embodiment

Figure 2:
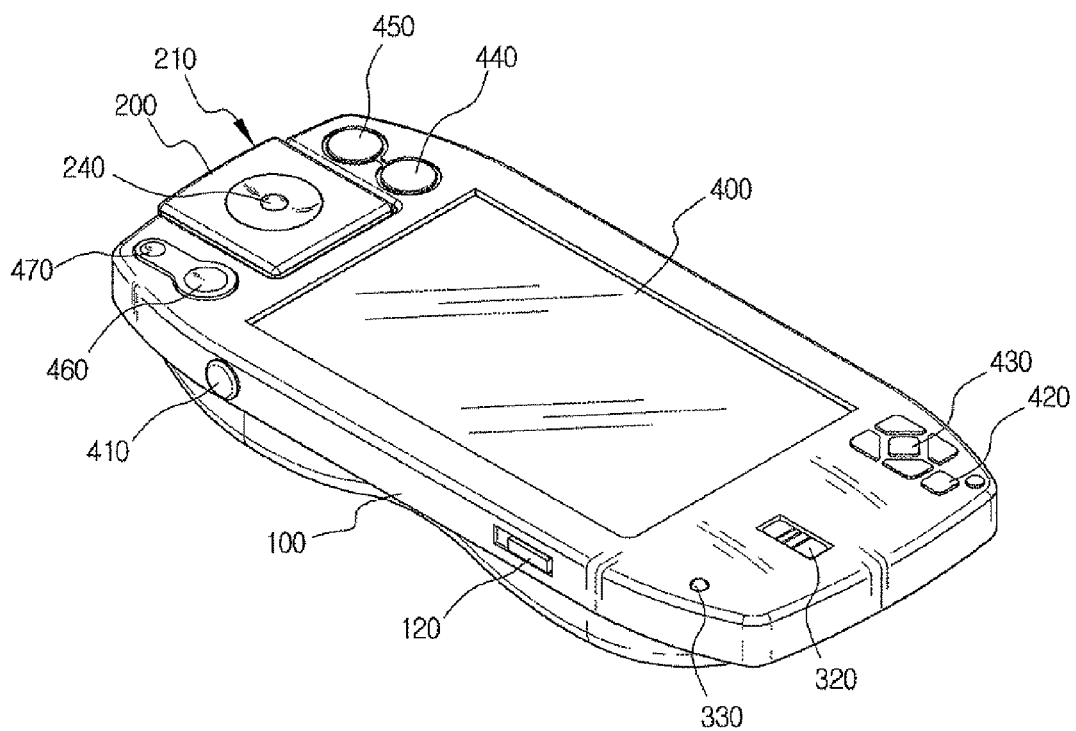
Figure 3:
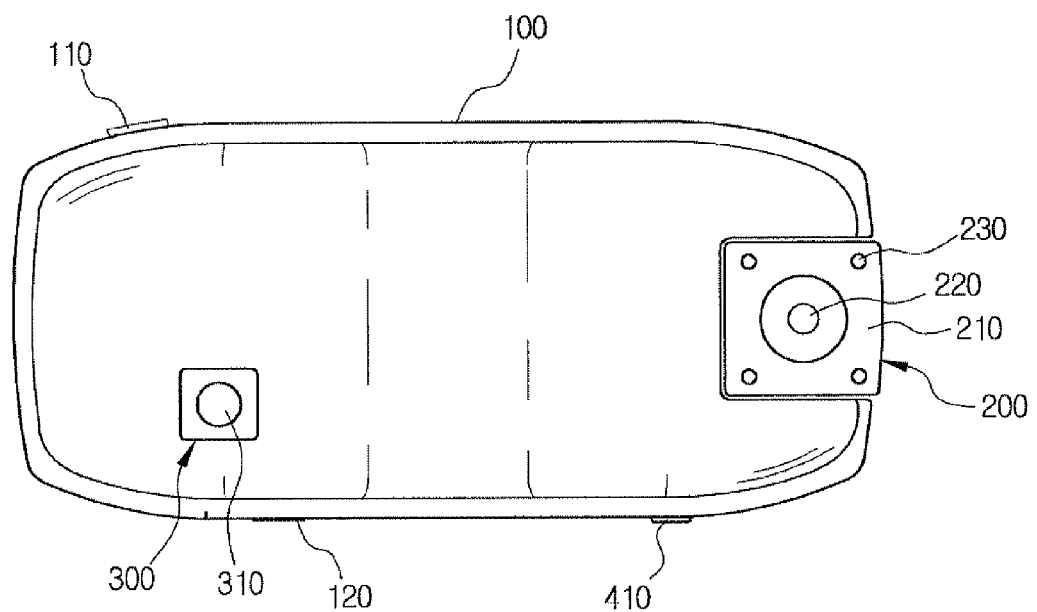
FIG. 3 is a bottom view of FIG. 1.
Figure 4:
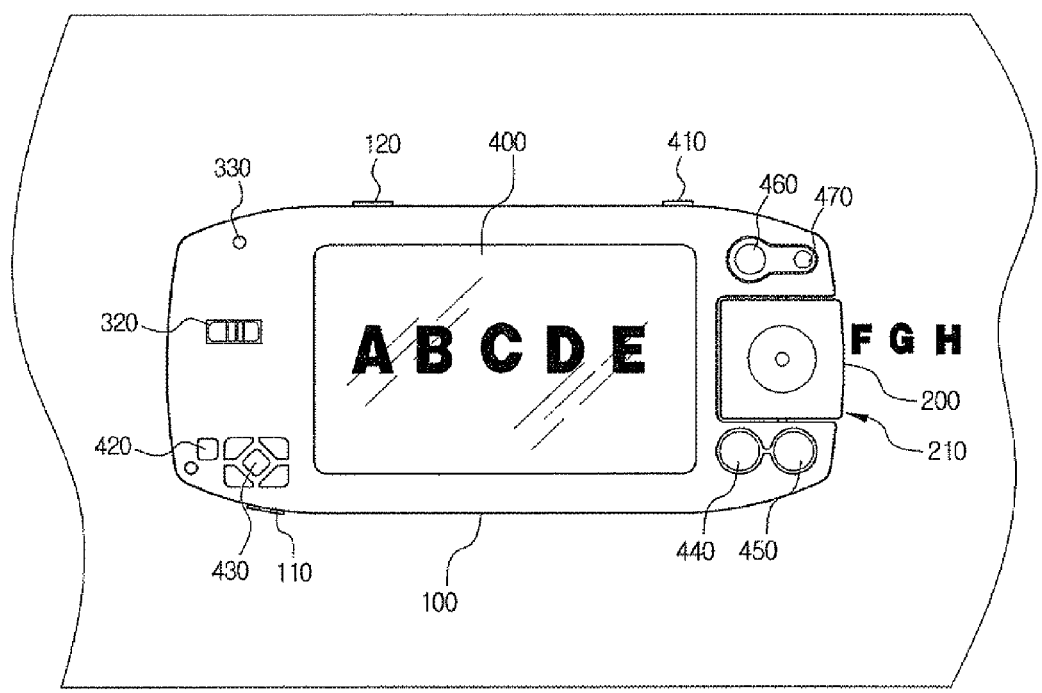
FIG. 4 is a view showing an example of an image output through a display part when a short distance image detecting part of the portable video magnifying apparatus is operated according to the first embodiment of the present invention.
Figure 5:
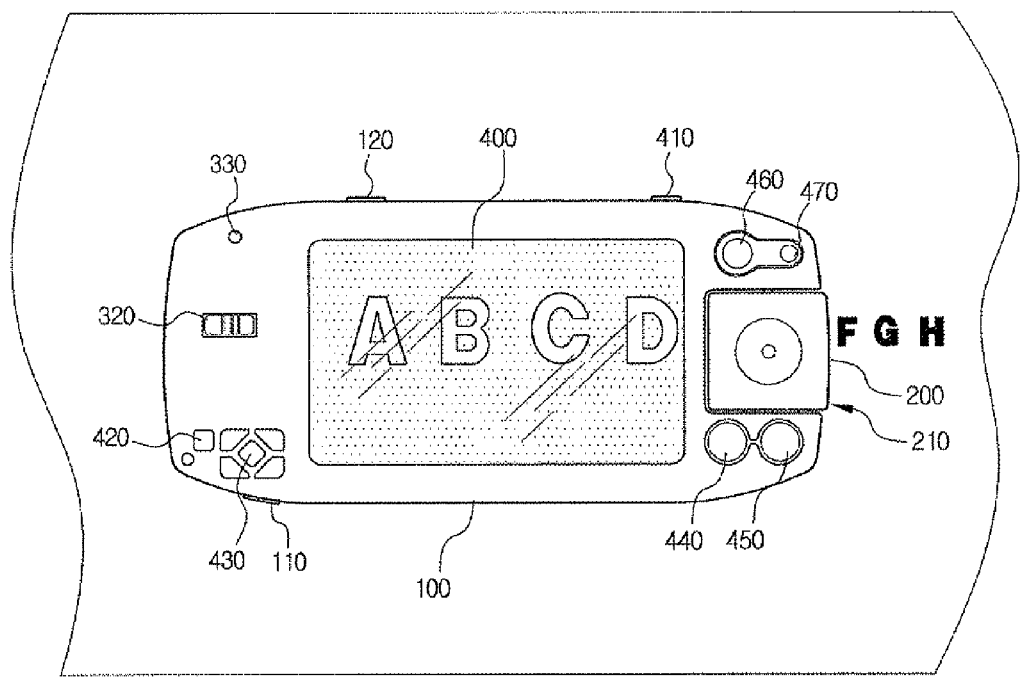
FIG. 5 is a view showing an example of an image output through the display part after a color of the image is converted.
Figure 6:
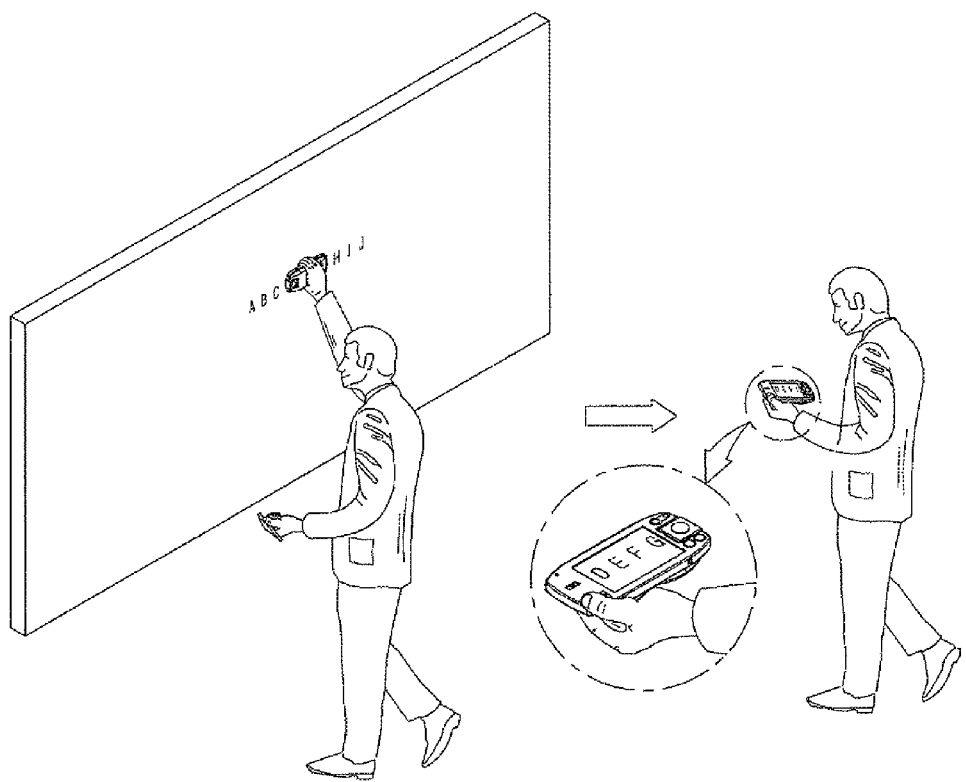
FIG. 6 is a view showing an example of image pausing/storing function for recognizing a subject positioned at a higher place than a user's eye level.
Figure 7:
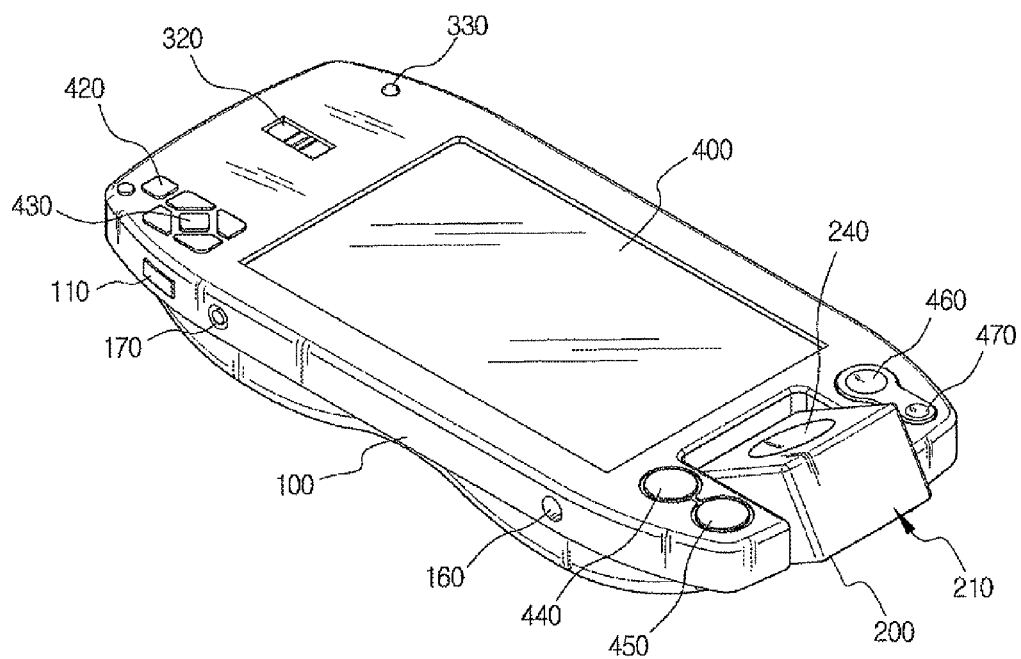
FIG. 7 is a view showing a state that an auxiliary frame 210 is pivoted in a writing mode of the portable video magnifying apparatus according to the first embodiment of the present invention.
Figure 8:
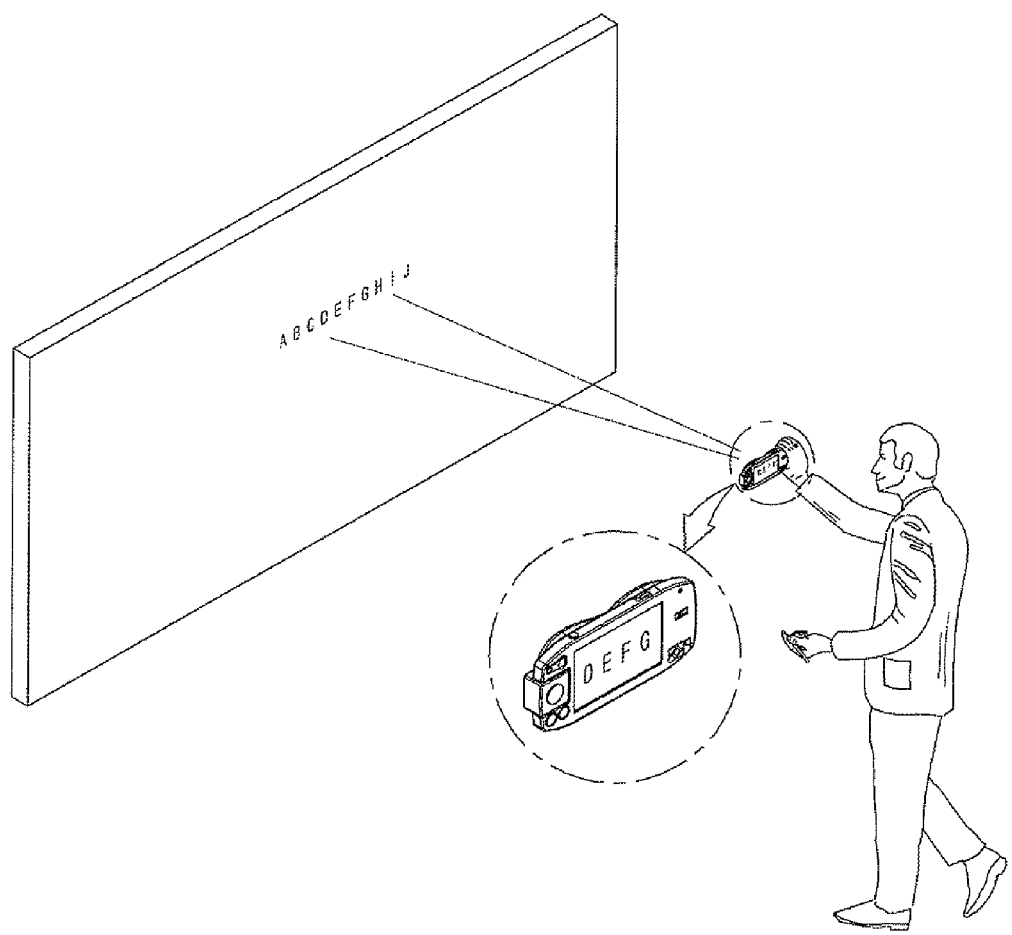
FIG. 8 is a view showing an example of an image output through the display part when a long distance image detecting part is operated according to the first embodiment of the present invention.
Figure 9:
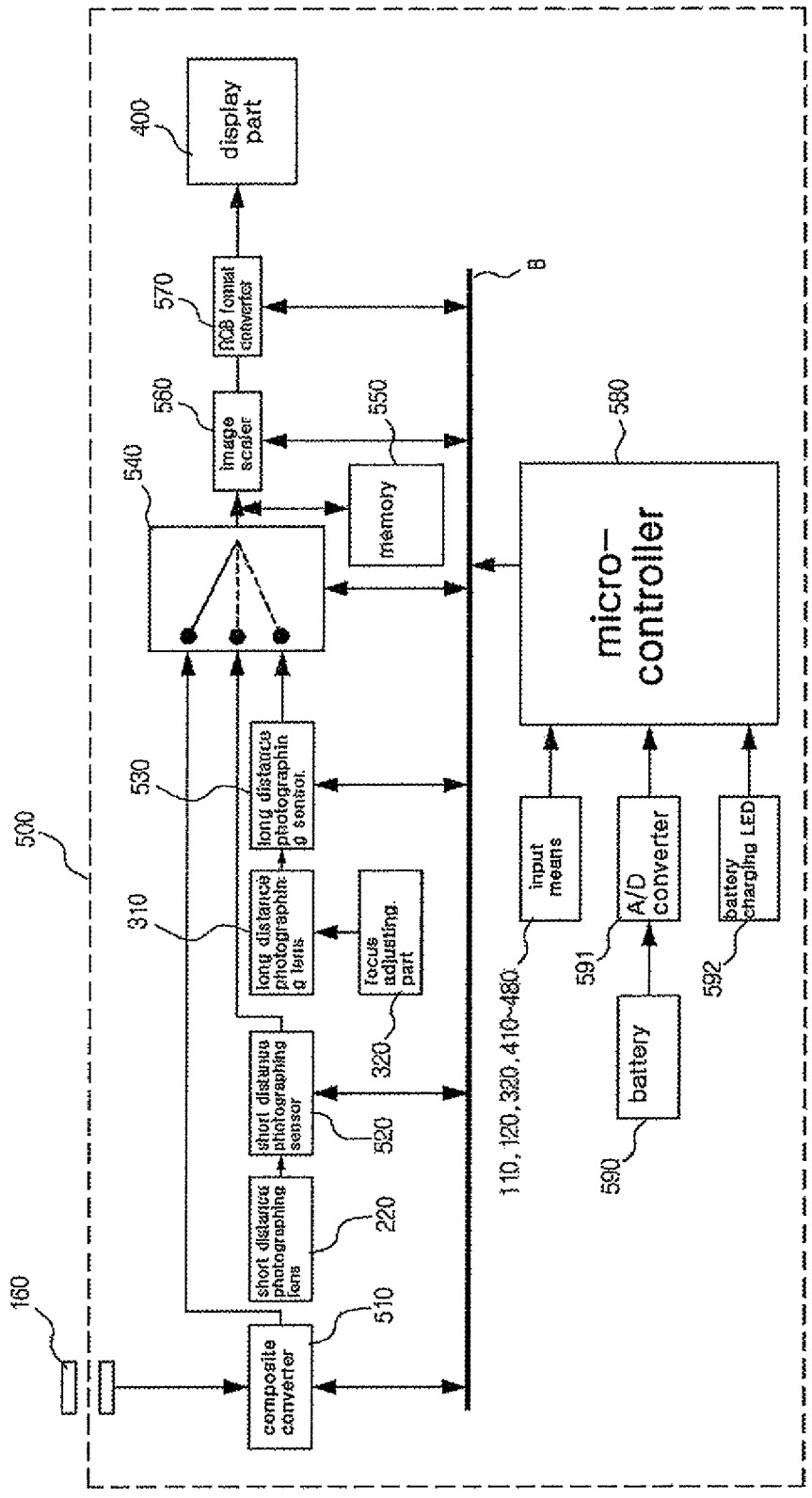
FIG. 9 is a block diagram showing a method of controlling the portable video magnifying apparatus according to the present invention.

FIGS. 1 and 2 are perspective views showing a portable video magnifying apparatus according to a first embodiment of the present invention, FIG. 3 is a bottom view of FIG. 1, FIG. 4 is a view showing an example of an image output through a display part when a short distance image detecting part of the portable video magnifying apparatus is operated according to the first embodiment of the present invention, FIG. 5 is a view showing an example of an image output through the display part after a color of the image is converted, FIG. 6 is a view showing an example of image pausing/storing function for recognizing a subject positioned at a higher place than a user's eye level, FIG. 7 is a view showing a state that an auxiliary frame 210 is pivoted in a writing mode of the portable video magnifying apparatus according to the first embodiment of the present invention, FIG. 8 is a view showing an example of an image output through the display part when a long distance image detecting part is operated according to the first embodiment of the present invention, and FIG. 9 is a block diagram showing a method of controlling the portable video magnifying apparatus according to the present invention.

Referring to FIGS. 1 to 3, a portable video magnifying apparatus according to a first embodiment of the present invention includes a main frame 100, a short distance image detecting part 200 which is pivotably disposed at the main frame 100, a long distance image detecting part 300 which is disposed at the main frame 100, and a display part 400.

The main frame 100 is provided with a composite input terminal 160 which is disposed at a desired position, a power input terminal 170 for power charging, a power switch 110 for turning on/off the portable video magnifying apparatus. If the power is charged through the power input terminal 170 and then applied to the portable video magnifying apparatus by the power switch 110, an image input through the short distance image detecting part 200 or the long distance image detecting part 300 is output through the display part 400. To help a user who has a narrow viewing angle, if TV is connected with the portable video magnifying apparatus through the composite input terminal 160 and the images are input through the TV, the short and long distance image is deactivated and the TV images are displayed through the display part 400.

According to the first embodiment of the present invention, the portable video magnifying apparatus has an image change detection function. Therefore, if the portable video magnifying apparatus is turned on and left alone for predetermined time, the fact that the image is not changed is detected and then the portable video magnifying apparatus is automatically turned off, thereby preventing unnecessary power consumption. The power switch 110 is slid from an initial position to a power-on position or a power-off position by external force. However, the power switch 110 is constructed so that it is arrived at the power-on or power-off position and then automatically returned to the initial position. In addition, the power switch 110 is also constructed so that the portable video magnifying apparatus can be automatically turned off, if the power switch 110 is slid to the power-on position and then returned to the initial position and the image is not changed for the predetermined time. In the first embodiment, since the portable video magnifying apparatus has the image change detection function and a power-off circuit, if the portable video magnifying apparatus is left alone for the predetermined time, the portable video magnifying apparatus is automatically turned off, thereby preventing the unnecessary power consumption. Therefore, in case that the portable video magnifying apparatus is automatically turned off by the image change detection function and the power-off circuit, since the power switch 110 is positioned at the initial position, the user can turn on the portable video magnifying apparatus by simply sliding the power switch 110 to the power-on position.

The short distance image detecting part 200 is pivotably disposed at the main frame 100 so as to photograph proximately a subject placed right under the main frame 100 or around there. Such the short distance image detecting part 200 includes an auxiliary frame 210 which is pivotably disposed at the main frame 100, a short distance photographing lens 220 which is disposed at the auxiliary frame 210 so as to photograph proximately a subject placed right under the main frame 100 or around, an illuminating LED 230 which is disposed around the short distance photographing lens 220 so as to illuminate the subject upon a photographing operation, and a short distance camera indicating lamp 240 which is disposed on an opposite surface of the short distance photographing lens 220 so as to inform the user of a position of the short distance photographing lens 220 and activation of the short distance image detecting part 200.

Referring to FIG. 4 or 7, the auxiliary frame 210 forms a horizontal plane together with the main frame 100. In a reading mode, while the portable video magnifying apparatus is positioned on the subject, the short distance photographing lens 220 is spaced away from the subject and then directed to the subject placed right under the main frame 100. In other words, in the reading mode, a surface on which the short distance photographing lens 220 is provided is kept to be parallel with a lower surface of the main frame 100, and the short distance photographing lens 220 is positioned at an upper side of the lower surface of the main frame 100.

Meanwhile, in a writing mode, the auxiliary frame 210 is pivoted at a desired angle so that the short distance photographing lens 220 is directed to the subject like letters which are being written near a location placed right under the main frame 100. That is, in the writing mode, the auxiliary frame 210 is pivoted at the desired angle so that the surface on which the short distance photographing lens 220 is disposed is directed to an outer side of the main frame 100. Generally, the pivot structure may be constructed to be manually pivoted by hinge coupling using a pivot shaft or a protrusion, or, if necessary, to be automatically pivoted by using a small motor and a control part for controlling the small motor. Therefore, the inconvenience that the user should obliquely take the main frame 100 so that the short distance photographing lens 220 is directed to the subject can be improved.

Image data output in the first embodiment is obtained by a CMOS camera which has smaller power consumption than a CCD camera. The short distance photographing lens 220 is formed of an aspheric lens in order to minimize a phenomenon that an image is distorted at outer sides of the image after adjusting a focus of the short distance photographing lens 220 of the short distance photographing lens 220. Since using the aspheric lens can minimizes a distance between the short distance photographing lens 220 and subject, it is possible to reduce an entire thickness of the portable video magnifying apparatus.

Referring to FIG. 8, the long distance image detecting part 300 is disposed at the main frame 100 so as to photograph a long distance subject. The long distance image detecting part 300 is provided at a desired position of the main frame 100, and includes a long distance photographing lens 310 for photographing the long distance subject, a focus adjusting part 320 which is rotated clockwise or counterclockwise so as to adjust a focus of the long distance photographing lens 310, and a long distance camera indicating lamp 330 which is disposed on an opposite surface of the long distance photographing lens 310 so as to inform the user of a position of long distance photographing lens 310 and activation of the long distance image detecting part 300. Herein, since the distance between the subject and the long distance photographing lens 310 is always changed, it is preferable that the focus of the long distance photographing lens 310 is controlled by the focus adjusting part 320 and the long distance photographing lens 310 is formed of a lens having a deep depth of field which can be focused in a certain region without the adjusting of the focus. Meanwhile, the long distance image detecting part 300 may further include an auto focusing part for automatically focusing the long distance photographing lens 310.

Referring to FIGS. 4 and 8, the display part 400 is formed of a color LCD and functions to output selected one out of the short distance image, the long distance image and the image input through the composite terminal 160. The display part 400 selectively outputs the short distance image or the long distance image by a camera selecting switch 120, and if other image is input through the composite input terminal 160, the short distance image or the long distance image is deactivated and the input image is displayed. Moreover, the display part 400 has various functions of color-converting, storing and magnifying the short distance image or the long distance image. For this end, the display part 400 includes an image pausing/storing button 410 which pauses or stores an image output through the display part 400, a menu button 420 which outputs icons for indicating functions of displaying a stored image, deleting the stored image, checking an image storing space, checking a battery residual capacity, scrolling a screen and the like, a icon selecting buttons 430 which selects the output icons and controls each function, a brightness adjusting button 440 which adjusts a brightness of the display part 400, a color converting button 450 which converts a color of the image into other color and then outputs the image having the converted color, and magnifying and reducing buttons 460 and 470 which control an magnification of the output image. If the image pausing/storing button 410 is pushed for a shorter time period than predetermined time, the image displayed on the display part 400 is paused, and if the image pausing/storing button 410 is pushed for a longer time period than the predetermined time, the image displayed on the display part 400 is stored in a memory. For example, the predetermined time may be set to 2~4 seconds. Referring to FIG. 6, the image pausing/storing button 410 is a functional button for recognizing the subject positioned at a higher place than the user's eye level. The user goes near the subject positioned at a higher place than the user's eye level, and photographs the subject using the short or long distance photographing lens 220 or 310, and then directly sees the subject through the display part 400 after placing the display part 400 near the user's eye. The stored images can be retrieved or deleted by using the menu button 420 and the icon selecting button 430. The menu button 420 and the icon selecting button 430 may be embodied together in a navigation button. Referring to FIG. 5, the color converting button 450 is provided for the user who is color-blind or color-weak, and functions to output the image of which colors are converted or reversed from an original image through the display part 400.

Hereinafter, referring to FIG. 9, a method of controlling a hardware system 500 of the first embodiment will be described.

The hardware system 500 includes a short distance photographing sensor 520 which converts an image detected from the short distance photographing lens 220 into a YUV type digital image signal and then outputs the digital image signal, a long distance photographing sensor 530 which converts an image detected from the long distance photographing lens 310 into the YUV type digital image signal and then outputs the digital image signal, a composite converter 510 which converts a composite signal input through the composite input terminal 160 into the YUV type digital image signal and then outputs the digital image signal, an image selector 540 which selects only one YUV signal when the above-mentioned three YUV image signals are input simultaneously, and a memory 550 which stores a signal selected by the image selector 540 and allows the user to see the image again when the user wants to do. Further, the hardware system 500 according to the first embodiment of the present invention may include an image scaler 560 which processes a signal input through the magnifying or reducing button 460 or 470 and performs an image magnifying function, and an RGB format converter 570 which performs a color converting function of an image and produces a processed image signal which is formatted to the display part 400. In addition, the image scaler 560 has the image change detection function. Therefore, if the portable video magnifying apparatus is left alone for the predetermined time period, the state is transferred to the power-off circuit and thus the power is cut off so as to prevent the unnecessary power consumption. Furthermore, there may be further provided an A/D converter 591 which A/D-converts a voltage of a battery 590 and then transfers the converted data to a micro-controller 580 so as to check a residual capacity of the battery 590. And a battery charging LED 592 allows the user to know a battery charging state even though the portable video magnifying apparatus is not turned on. The composite converter 510, the short distance photographing sensor 520, the long distance photographing sensor 530, the image selector 540, the image scaler 560 and the RGB format converter 570 are electrically connected through a BUS B to the micro-controller 580. Therefore, if the user inputs information to the micro-controller 580 by using an input means like the various buttons and switches 110, 120, 320, 410, 420, 430, 440, 450, 460, 470 and 480, the information is transferred through the BUS B to each part so that the various functions are performed.

Second Embodiment

Figure 10:
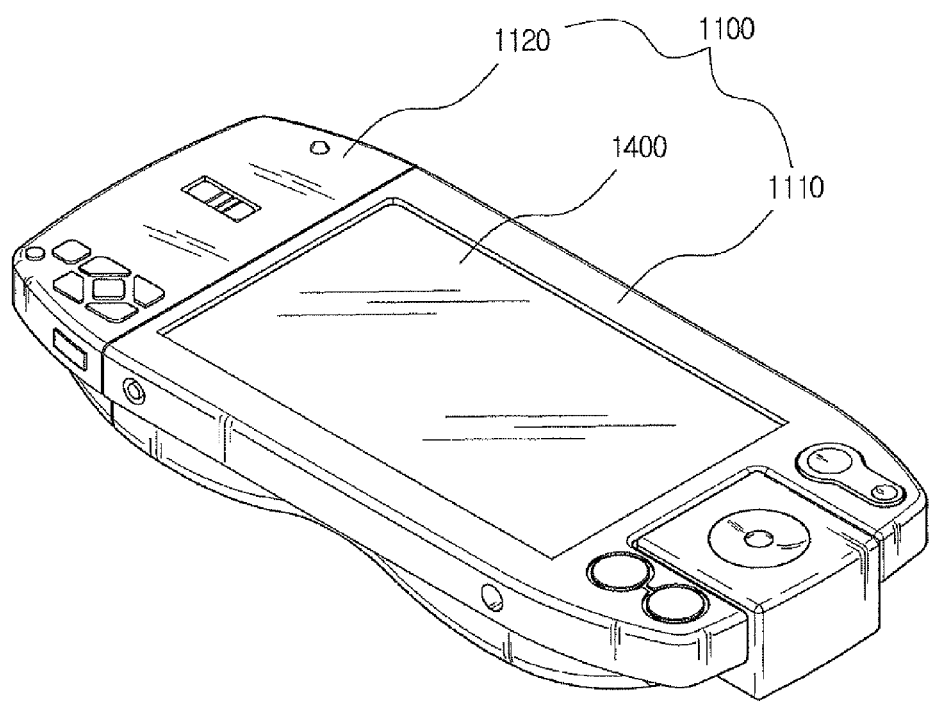
FIG. 10 is a perspective view showing a portable video magnifying apparatus according to a second embodiment of the present invention.

A second embodiment is another example of the portable video magnifying apparatus according to the present invention. FIG. 10 is a perspective view showing a portable video magnifying apparatus according to a second embodiment of the present invention, and FIG. 11 is a view showing an operation state of the portable video magnifying apparatus according to the second embodiment of the present invention.

Some descriptions in the second embodiment, which are insufficient or not described, are correspondent to the first embodiment.

Referring to FIG. 10, the portable video magnifying apparatus according to the second embodiment of the present invention is provided with a main frame 1100 which is divided into a first main frame 1110 and a second main frame 1120.

Figure 11:
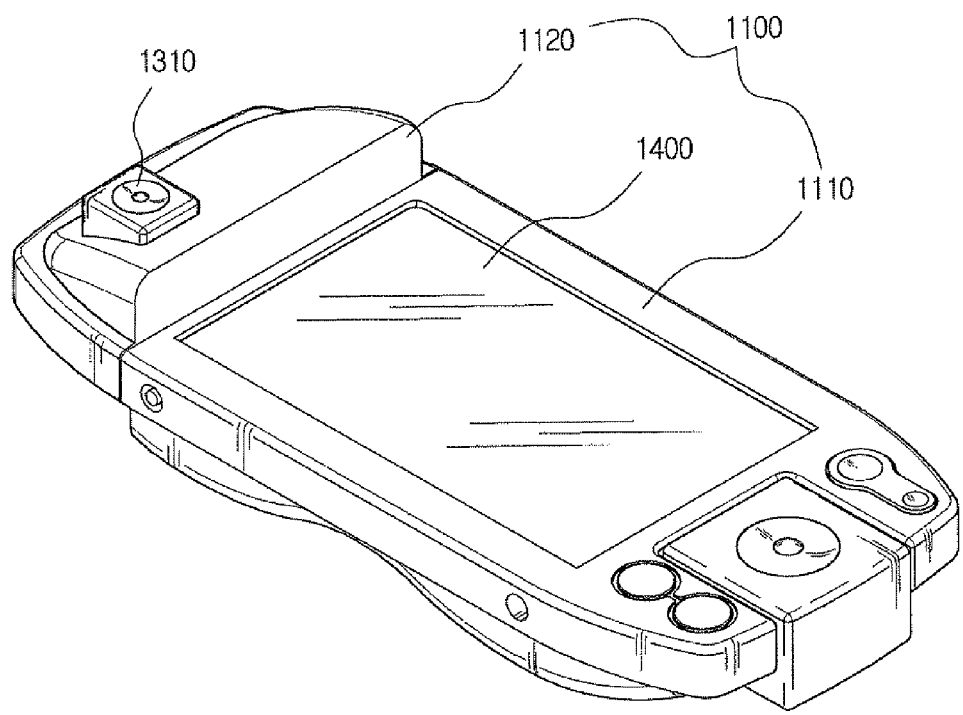
FIG. 11 is a view showing an operation state of the portable video magnifying apparatus according to the second embodiment of the present invention.

A display part 1400 is disposed at the first main frame 1110, as shown in FIG. 10, and a long distance photographing lens 1310 is disposed at the second main frame 1120, as shown in FIG. 11.

Referring to FIGS. 10 and 11, the second main frame 1120 is rotatably coupled to one end of the first main frame 1110. The second main frame 1120 can be rotated at an angle of at least 180° so that the long distance photographing lens 1310 is directed to an upper or lower surface of the first main frame 1110. In other words, the second main frame 1120 is rotated with respect to the first main frame 1110, so that the long distance photographing lens 1310 can photograph a subject positioned in an upper or lower direction of the display part 1400.

Therefore, unlike in the first embodiment, there is an advantage that it is possible to photograph the subject positioned in the upper or lower direction of the display part 1400 without changing a direction of the display part 1400.

Further, in a state that a short distance image detected by a short distance image detecting part is displayed on the display part 1400, if the second main frame 1120 is rotated with respect to the first main frame 1110, a long distance image detected by a long distance image detecting part is displayed on the display part 1400.

Meanwhile, although not shown in drawings, the second main frame 1120 may be constructed so as to be rotated with respect to the first main frame 1110 at a predetermined angle and then halted. Thus, the user is allowed to photograph the subject positioned at an optional place on a plane perpendicular to the display part 1400 by fixing the display part 1400 of the first main frame 1110 within a visual field and rotating and halting the first main frame 1110 at the predetermined angle.

In the second embodiment, the second main frame 1120 may be also constructed so as to be rotated and halted with respect to the first main frame 1110 at a first predetermined angle and then to be rotated again and halted with respect to the first main frame 1110 at a second predetermined angle. For example, the second main frame 1120 can be rotated and halted at 10°, and then further rotated and halted at another 10°.

Referring to FIG. 10, in the second embodiment, the second main frame 1120 is coupled to a lower end of the first main frame 1110. However, the second main frame 1120 may be coupled to a left or right end of the first main frame 1110. Further, the second main frame 1120 may be disposed in a through-groove which is formed pass through the upper and lower surfaces of the first main frame 1110.

Moreover, the second main frame 1120 may be disposed in a through-hole passing through the upper and lower surface of the first frame 1110. And, the second main frame 1120 can be rotated at an angle of at least 180° so that the long distance photographing lens 1310 is directed to the upper or lower surface of the first main frame 1110. However, the rotational angle of the second main frame 1120 with respect to the first main frame 1110 may be smaller than 180°.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

INDUSTRIAL APPLICABILITY

According to the present invention, as described above, since the long or short distance image is magnified and then displayed through the display part, it is possible to help the weak-sighted or aged person. Therefore, the present invention can be used in the manufacturing field of the portable video magnifying apparatus.

The invention claimed is:

1. A portable video magnifying apparatus, comprising:
   a main frame;
   a short distance image detecting part which is pivotably disposed at the main frame so as to photograph proximately a subject right placed under the main frame or around there;
   a long distance image detecting part which is provided with a long distance photographing lens for photographing a long distance subject and which is disposed at the main frame; and
   a display part which outputs one out of the short distance image, the long distance image and an image input through an external portion, which is selected by a user,
   wherein the long distance image detecting part comprises:
   a focus adjusting part which is rotated clockwise or counterclockwise so as to adjust a focus of the long distance photographing lens; and
   a long distance camera indicating lamp which is disposed on an opposite surface of the long distance photographing lens so as to inform the user of activation of the long distance image detecting part.

2. The portable video magnifying apparatus according to claim 1, wherein the short distance image detecting part comprises:
   an auxiliary frame which is pivotably disposed at the main frame;
   a short distance photographing lens which is disposed at the auxiliary frame so as to photograph proximately a subject placed right under the main frame or around;
   an illuminating LED which is disposed around the short distance photographing lens so as to illuminate the subject upon a photographing operation; and
   a short distance camera indicating lamp which is disposed on an opposite surface of the short distance photographing lens so as to inform the user of activation of the short distance image detecting part.

3. The portable video magnifying apparatus according to claim 2, wherein the auxiliary frame is positioned in a reading mode so that a surface thereof having the short distance photographing lens is placed at an upper side of a lower surface of the main frame, and the auxiliary frame is rotated at a desired angle in a writing mode so that the surface thereof having the short distance photographing lens is directed to an outer side of the main frame.

4. The portable video magnifying apparatus according to claim 1, wherein the long distance image detecting part further comprises an auto focusing part for automatically focusing the long distance photographing lens.

5. The portable video magnifying apparatus according to claim 1, wherein the display part comprises:
- an image pausing/storing button which pauses or stores an image output through the display unit;
- a menu button which outputs icons for indicating functions of displaying a stored image, deleting the stored image, checking an image storing space, checking a battery residual capacity, and scrolling a screen; and
- a icon selecting buttons which selects the output icons.

6. The portable video magnifying apparatus according to claim 1, wherein the display part further comprises:
- a brightness adjusting button which adjusts a brightness of the display part;
- a color converting button which converts a color of the image into other color and then outputs the image having the converted color; and
- magnifying and reducing buttons and which controls an magnification of the output image.

7. The portable video magnifying apparatus according to claim 1, wherein, if the image pausing/storing button is pushed for a shorter time period than predetermined time, the image displayed on the display part is paused, and if the image pausing/storing button is pushed for a longer time period than the predetermined time, the image displayed on the display part is stored in a memory.

8. The portable video magnifying apparatus according to claim 1, wherein the main frame is provided with a power switch for turning on/off the portable video magnifying apparatus, and the power switch is automatically slid from a power-on position or a power-off position to an initial position, and the power switch is also constructed so that the portable video magnifying apparatus can be automatically turned off, if the power switch is slid to the power-on position and then returned to the initial position and the image is not changed for a predetermined time.

9. The portable video magnifying apparatus according to claim 1, wherein the main frame is provided with a composite input terminal and a camera selecting switch, and the display part selectively displays a short or long distance image by the camera selecting switch, and if an image is input through the composite input terminal, the short or long distance image is deactivated and the input image is displayed through the display part.

10. The portable video magnifying apparatus according to claim 1, wherein the main frame comprises a first main frame in which the display part is provided, and a second main frame in which the long distance photographing lens is provided, and the second main frame is rotatably coupled to the first main frame so that a photographing direction of the long distance photographing lens can be changed.

11. The portable video magnifying apparatus according to claim 10, wherein the second main frame can be rotated at an angle of at least 180° so that the long distance photographing lens is directed to an upper or lower surface of the first main frame.

12. The portable video magnifying apparatus according to claim 10, wherein, if the second main frame is rotated while the short distance image from the short distance image detecting part is displayed through the display part, a long distance image from the long distance image detecting part is displayed through the display part.

13. The portable video magnifying apparatus according to claim 10, wherein the second main frame is coupled to an end of the first main frame.

14. The portable video magnifying apparatus according to claim 1, wherein the second main frame is rotated with respect to the first main frame at a predetermined angle and then halted.

* * * * *